US006926713B2

(12) United States Patent
Rioux et al.

(10) Patent No.: US 6,926,713 B2
(45) Date of Patent: Aug. 9, 2005

(54) ANGLE INDEXER FOR MEDICAL DEVICES

(75) Inventors: Robert F. Rioux, Ashland, MA (US); Christopher J. Elliott, Hopkinton, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 205 days.

(21) Appl. No.: 10/317,796

(22) Filed: Dec. 11, 2002

(65) Prior Publication Data

US 2004/0116920 A1 Jun. 17, 2004

(51) Int. Cl.[7] .............................................. A61B 18/18
(52) U.S. Cl. ...................................................... 606/41
(58) Field of Search .................................... 606/27–52

(56) References Cited

U.S. PATENT DOCUMENTS

| | | | |
|---|---|---|---|
| 4,565,200 A | 1/1986 | Cosman | |
| 5,855,576 A | 1/1999 | LeVeen et al. | |
| 5,989,247 A | * 11/1999 | Chambers | ..................... 606/41 |
| 6,315,777 B1 | 11/2001 | Comben | |
| 6,622,731 B2 | * 9/2003 | Daniel et al. | ............... 128/898 |
| 2001/0034518 A1 | 10/2001 | Edwards et al. | |
| 2002/0065541 A1 | 5/2002 | Fredricks et al. | |

FOREIGN PATENT DOCUMENTS

WO    WO 96/29946    10/1996

\* cited by examiner

*Primary Examiner*—Roy D. Gibson
*Assistant Examiner*—Pete Vrettakos
(74) *Attorney, Agent, or Firm*—Bingham McCutchen LLP

(57) ABSTRACT

Ablation device for creating a lesion within tissue includes an angle indexing apparatus. The angle indexing apparatus includes an index-key and an indexer. The index-key is secured to the ablation device. The indexer is secured in a position relative to which the index-key can move. The index-key is adapted to mate with the indexer in a plurality of positions, thereby allowing operation of the ablation device in a plurality of orientations.

24 Claims, 8 Drawing Sheets

ANGLE INDEXER FOR MEDICAL DEVICES

BACKGROUND OF THE INVENTION

1. Field of the Invention

The present invention relates generally to the structure and use of radio frequency electrosurgical probes for the treatment of tissue. More particularly, the present invention relates to an electrosurgical probe having multiple wire electrodes which are deployed in an array to treat a volume of tissue, particularly for tumor treatment.

2. Background of the Invention

The treatment of bodily tissue by using thermal energy to destroy it is useful for various therapeutic procedures. Thermal energy can be imparted to tissue using radio frequency electrical energy, microwave or lightwave electromagnetic energy, ultrasonic vibrational energy, or thermal conduction.

Radiofrequency ablation (RFA) is becoming a popular medical alternative to treat patients with tissue anomalies who were previously not candidates for surgery. For example, RFA is commonly used to treat liver anomalies and many primary cancers, such as cancers of the stomach, bowel, pancreas, kidney and lung. RFA treatment involves the destruction of undesirable cells by generating heat through agitation caused by the application of alternating electrical current (radiofrequency energy) through the tissue.

Various RF ablation devices have been designed to perform this treatment. See, for example, U.S. Pat. No. 5,855,576, which describes an ablation apparatus that includes a plurality of wires connected through a catheter. Each of the wires includes a proximal end that is connected to a generator, and a distal end projecting from a distal end of the catheter. The wires are arranged in an array with the distal ends located generally radially and uniformly spaced apart from the catheter distal end. The wire ends act as electrodes that may be energized in a monopolar or bipolar fashion to heat and necrose tissue within a precisely defined volumetric region of target tissue. The current can flow between closely spaced energized wire electrodes or between an energized wire electrode and a larger, common electrode located remotely from the tissue to be heated. In order to assure that the target tissue is adequately treated and limit damage to adjacent healthy tissues, it is desirable that the array formed by the wires within the tissue be precisely and uniformly defined. In particular, it is generally desirable that the independent wires be evenly and symmetrically spaced-apart so that heat is generated uniformly within the desired target tissue volume. The ablation device may be used either in an open surgical setting, in laparoscopic (small incision) procedures, or in percutaneous (through the skin) interventions.

During ablation of tissue, the maximum heating often occurs in the local tissue, immediately adjacent the emitting electrodes. In general, the level of tissue heating is proportional to the square of the electrical current density, and the electrical current density in tissue generally falls as the square of the distance from the electrode. Therefore, the heating in tissue generally falls as the fourth power of distance from the electrode and the resulting tissue temperature therefore decreases rapidly as the distance from the electrode increases. This causes a lesion to first form along the electrodes, and then between the electrodes.

For example, FIGS. 1A to 1D show how a desired thermal lesion is created using the above described ablation apparatus. Using conventional imaging methods such as ultrasound, an array 2 of wires 4 is positioned strategically within the targeted area of tissue and energized with electrical current. Initially, a thermal lesion 6 begins to form at the tips of the wires 4 (FIG. 1A). As the ablation process continues, the thermal lesion 6 expands along the wires 4 back toward the center of the array 2, as indicated by the directional arrow 7 (FIG. 1B). Next, the thermal lesion 6 expands outward and between the wires 4, as indicated by the directional arrow 8 (FIG. 1C), until the desired thermal lesion 6 is formed (FIG. 1D).

Due to physical changes within the tissue during the ablation process, the desired thermal lesion 6 illustrated in FIG. 1D is typically difficult to achieve in a single RF application. For example, the concentration of heat adjacent the wires 4 often causes the local tissue to desiccate, thereby reducing its electrical conductivity. As the tissue conductivity decreases, the impedance to current passing from the electrode to the tissue increases so that more voltage must be supplied to the electrodes to affect the surrounding, more distant tissue. The tissue temperature proximate to the electrode may approach 100° C., so that water within the tissue boils to become water vapor. As this desiccation and/or vaporization process continues, the impedance of the local tissue may rise to the point where a therapeutic level of current could no longer pass into the surrounding tissue.

Thus, the rapid fall-off in tissue temperature ultimately limits the volume of tissue that can be therapeutically treated by each of the wire electrodes. As such, depending on the rate of heating and how far the wire electrodes are spaced from each other, ablation devices that have multiple spreading wires may fail to create complete and uniform lesions. While wire electrodes can be repeatedly repositioned to treat additional tissue, the precise movement required for this task is difficult to accomplish.

For these reasons, it would be desirable to provide improvements to ablation devices, such as, e.g., those described in U.S. Pat. No. 5,855,576, so that they could create complete or more uniform lesions.

SUMMARY OF THE INVENTION

In accordance with a first aspect of the present inventions, a medical device comprises an elongate member having a proximal end and a distal end, and an operative element carried at the distal end of the elongate member. By way of non-limiting example, the medical device can be an ablation device, and the operative element can be one or more electrodes, e.g., a needle electrode array. The medical device, however, can include other types of medical devices, including diagnostic devices, and the operative element can include in one or more of variety of instruments, such as sensors, cutting devices, mapping instruments, embolic devices, or delivery devices. Depending upon the medical application, the elongate member can take the form of any mechanism that facilitates delivery of the operative element to a desired target area within or on the patient's body, and thus can be rigid, semi-rigid, or flexible.

The medical device further comprises an indexer and an index-key secured to the elongate member, wherein the index-key is adapted to mate with the indexer in at least two fixed rotational positions. In the preferred embodiment, the index-key is secured to the proximal end of the elongate member, but can be secured anywhere along the elongate member, including its distal end, that allows mating with the indexer. The medical device may optionally include a handle at the proximal end of the elongate member, in which case, the index-key can be secured to the handle. In preferred embodiments, the index-key can fit within the indexer, or the indexer can fit within the index-key.

By way of non-limiting example, one of the indexer and index key has at least two keyways, and the other of the indexer and index key has at least one key element adapted to mate with each of the keyways. For example, the index key can have a single key element, and the indexer can have two keyways. Or the index key can have two key elements, and the indexer can have four keyways. Whatever the number, the keyways can lie along radial lines that define one or more angles in order to define the angle between the two fixed rotational positions of the index-key. For example, if the operative element is a needle electrode array that comprises two or more wires, these wires can be placed in first positions when the index key is mated with the indexer in the first rotational position, and placed in second positions when the index key is mated with the indexer in the second rotational position, such that the first positions are substantially midway between the second positions. Although the present inventions should not necessarily be so limited, it can be appreciated that operation of the operative element is more controlled. In the case of an ablation device, delivery of ablation energy may be more controlled, resulting in more desirable and uniform lesions.

In one preferred embodiment, the medical device comprises a tubular element having a lumen in which the elongate member is slidable. In this case, the indexer can be secured to the tubular element, e.g., to its proximal end and/or within its interior or exterior surface. Instead of securing the indexer to a device, such as the tubular element, the indexer may optionally be adapted to be secured to the patient or be hand-held by an operator.

In accordance with a second aspect of the present inventions, an angle indexing apparatus for positioning a medical device in a plurality of orientations comprises an index-key configured for coupling to the medical device, and an indexer securable in a position relative to which the index-key can move, wherein the index-key is adapted to mate with the indexer in at least two fixed rotational orientations. The index-key and indexer may operate with each other and have characteristics similar to that described above. The index-key can either be configured to be permanently affixed or detachably affixed to the medical device.

In accordance with a third aspect of the present inventions, a method for performing a medical procedure on a target tissue using a medical device is provided. The medical device has an elongate member and at least one operative element carried at the distal end of the elongate member. The method comprises advancing the elongate member such that the operative element(s) is adjacent the target tissue, e.g., in contact with the tissue. If a tubular element is provided, the elongate member can be advanced within the tubular element. The method further comprises affixing the elongate member in a first rotational orientation. For example, if the medical device comprises an index key that is secured to the elongate member and an indexer, the elongate member can be affixed in the first rotational orientation by engaging the index-key with the indexer in a first rotational position. The method further comprises operating the operative element(s) while adjacent the target tissue. By way of non-limiting example, if the operative element is an electrode, operation of the electrode can include delivering ablation energy to create a first lesion. The method further comprises affixing the elongate member in a second rotational orientation different from the first rotational orientation. Again, if an index-key and indexer are provided, the elongate member can be affixed in the second rotational orientation by disengaging the index-key from the indexer in the first rotational position, and reengaging the index-key with the indexer in the second rotational position. In the preferred embodiment, disengagement of the index-key from the indexer can simply require axially translating the index-key relative to the indexer. If the operative element is an electrode, operation of the electrode a second time can include delivering ablation energy to create a second lesion. The first and second lesions may be centered on each other.

In accordance with a fourth aspect of the present inventions, a method for performing a medical procedure on a target tissue is provided. The method comprises securing an index-key to a medical device having at least one operative element, securing an indexer in a position relative to which the index-key can move, engaging the index-key with the indexer in a first position, thereby positioning the operative element(s) adjacent a first region of the target tissue, operating the operative element(s) while adjacent the first region, engaging the index-key with the indexer in a second position, thereby positioning the operative element(s) adjacent a second region of the target tissue, and again operating the at least one operative element while adjacent the second region. In the case where the operative element is an electrode, ablation energy can be delivered to ablate the first region, and again delivered to ablate the second region. In the preferred method, the index-key can be disengaged from the indexer by axially translating the index-key relative to the indexer.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1A:
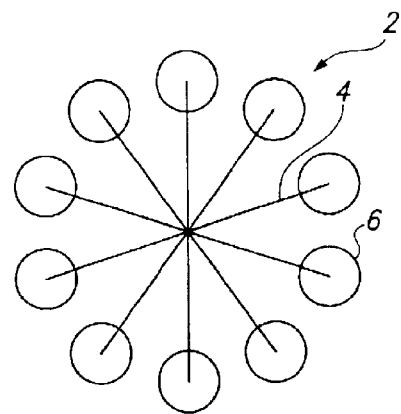
FIGS. 1A–1D shows various phases of a prior art lesion formation process using an ablation device having multiple wires.
Figure 1B:
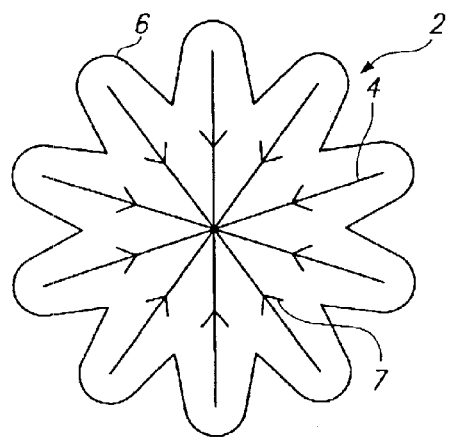
Figure 1C:
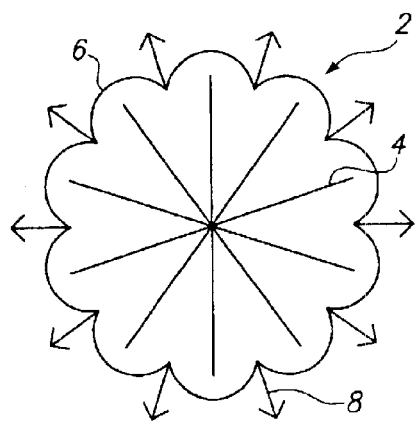
Figure 1D:
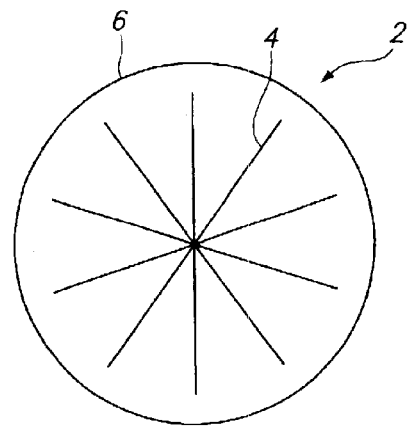
Figure 2:
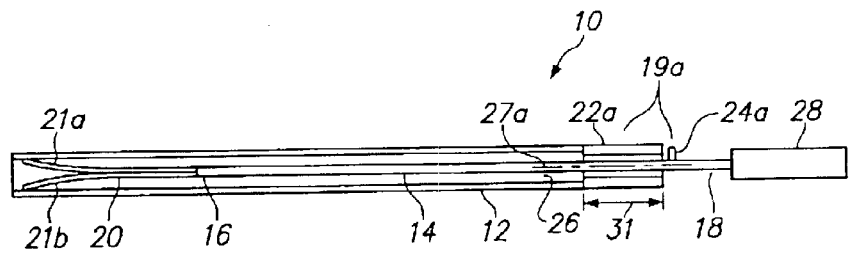
FIG. 2 is a side cross sectional view of a probe assembly that includes an angle indexing apparatus in accordance with a first preferred embodiment of the present invention.

Referring to FIG. 2, a probe assembly 10 constructed in accordance with a first preferred embodiment of the present invention is shown. The probe assembly 10 includes a tubular element, such as a cannula 12, an elongate member, such as a shaft 14, having a distal end 16 and a proximal end 18, an operative element 20 carried on the distal end 16 of the shaft 14, and an angle indexing apparatus 19. The angle indexing apparatus 19 includes an indexer 22a mounted to the proximal end of the cannula 12, and an index-key 24a mounted to the proximal end 18 of the shaft 14. As used in this specification, the index-key 24 refers to the component of the indexing apparatus 19 that is coupled to (and therefore, associated with) the shaft, or other part(s) of the probe assembly that carries the operative element 20. The shaft 14 is coaxially surrounded by the cannula 12 and is capable of being advanced or retracted coaxially within a lumen 26 of the cannula 12. The probe assembly 10 optionally includes a handle 28 connected to the proximal end 18 of the shaft 14. A marker (not shown) may also optionally be placed at the handle 28 or at the proximal end 18 of the shaft 14 for indicating the orientation of the shaft 14 and the operative element 20. The probe assembly 10 may also optionally include a sensor, such as a temperature sensor or an impedance sensor (not shown), carried at the distal end of the shaft 14.

The cannula 12 may be made of a variety of materials, including, but not limited to, plastics, metals, and polymers. Preferably, the cannula 12 is rigid, i.e., by being made of a stiff material, or by being reinforced with a coating or coil, to provide axial strength. The outer diameter of the cannula 12 is preferably less than ½ inch. However, other dimensions for the outer diameter of the cannula 12 may also be appropriate, depending on the particular application or clinical procedure. The cannula 12 should have an inner diameter that allows the shaft 14 to be inserted and slid within the lumen 26 of the cannula 12.

The shaft 14 is preferably rigid and is composed of a metal. However, the shaft 14 may also be made of other materials, including, but not limited to plastics, nitinol, titanium, methacrylates, and alloys. The shaft 14 preferably has a circular cross section. Alternatively, the shaft 14 may have other cross sectional shapes, such as square, rectangle, or customized shapes.

In the preferred embodiment shown in FIG. 2, the operative element 20 includes a plurality of electrically conductive wires 21 that are secured at a proximal end, forming an electrode array. In particular, the proximal ends of the wires 21 are preferably secured to the distal end 16 of the shaft 14, e.g., by welding, brazing, glue, screws, or other mechanical connections. If the shaft 14 has a lumen (not shown) extending between the distal end 16 and the proximal end 18 of the shaft 14, conductive wires for supplying energy to the wires 21 can be housed within the lumen. Alternatively, if the shaft 14 has a solid cross section, the conductive wires for supplying energy to the wires 21 can be housed within the lumen 26 of the cannula 12 and outside the shaft 14.

Figure 3:
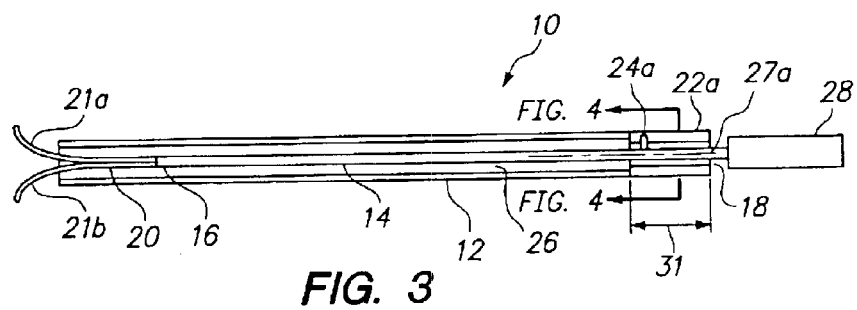
FIG. 3 is a side cross sectional view of the probe assembly of FIG. 2, particularly showing the wires deployed at the distal end of the cannula.

As shown in FIG. 2, the array of wires 21 is stretched into a low profile when the array of wires 21 is housed within the lumen 26 of the cannula 12. As FIG. 3 illustrates, advancing the proximal end 18 of the shaft 14, or the handle 28 if one is provided, pushes the wires 21 out of the lumen 26 of the cannula 12. When the wires are unconfined by the cannula 12, they assume a relaxed expanded configuration. FIG. 3 shows that a two-wire array is formed with each wire 21a, 21b arching in a general "U" shape and with each wire substantially uniformly separated. Alternatively, each wire 21a, 21b may have other shapes, such as a "J" shape, and the array may have just one wire or more than two wires. The wires 21 are preferably formed of spring wire or other material which will retain memory. During use of the probe assembly 10, the wires 21 are deployed into a target tissue, and deliver ablation energy to the tissue to create a lesion. Ablation devices having a spreading array of wires have been described in U.S. Pat. No. 5,855,576, the entirety of which is expressly incorporated by reference herein.

The indexer 22a is preferably made of plastic or polymer, but can also be made of other materials, such as metals. The indexer 22a is preferably separately manufactured from the cannula 12, and is then subsequently detachably coupled to the proximal end of the cannula 12. For such purpose, a luer-type connection may be used as the securing mechanism between the indexer 22 and the proximal end of the cannula 12. Alternatively, the securing mechanism may be a friction-type connection, or a screw-type connection, as are commonly known to those skilled in the art. The indexer 22a may also be permanently secured to the proximal end of the cannula 12 by welding, brazing, glue, or other types of adhesive, depending on the materials from which the indexer 22a and the cannula 12 are made. Even more alternatively, the indexer 22a can be fabricated together with the cannula 12 as one single component.

Figure 4:
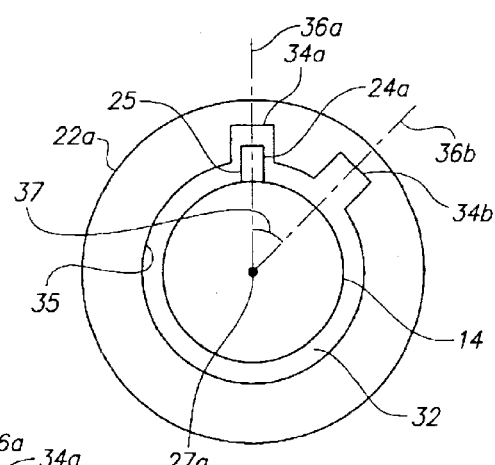
FIG. 4 is a cross sectional view of the probe assembly of FIG. 2, particularly showing the index-key mated with the indexer.

The index-key 24a is secured to the shaft 14 and includes a single key element 25 (shown in FIG. 4). The index-key 24a is preferably fabricated together with the shaft 14. Alternatively, the index-key 24a can be separately manufactured from the shaft 14, and then secured to the shaft 14 by welding, brazing, glue, or other suitable adhesives. The index-key 24a can also be secured within a pre-made opening located along the body of the shaft 14.

Referring further to FIG. 4, indexer 22a preferably has a circular exterior profile. Alternatively, the indexer 22a can have other exterior profiles, such as oval or rectangular. The indexer 22a includes a bore 32 at the center through which the shaft 14 can be inserted into the cannula 12. The profile of the interior surface 35 of the indexer 22a is preferably circular, defining a circular shaped bore 32. However, the profile of the interior surface 35 of the indexer 22a can have other shapes, so long as the indexer 22a allows the shaft 14 to be inserted into the bore 32 in two positions, as will be described below.

The indexer 22a includes two keyways 34a and 34b located on the interior surface 35 of the indexer 22a. The keyways 34a and 34b are located along respective radial lines 36a and 36b, which form an angle 37 therebetween. The index-key 24a is adapted to mate with the indexer 22a, such that when the shaft 14 is inserted into the lumen 26 of the cannula 12, the key element 25 of the index-key 24a fits within one of the keyways 34a and 34b of the indexer 22a. Particularly, when the key element 25 of the index-key 24 fits within the keyway 34a of the indexer 22a, the shaft 14 is guided to slide within the lumen 26 of the cannula 12 in a first rotational orientation. When the key element 25 of the index-key 24 fits within the keyway 34b of the indexer 22a, the shaft 14 is guided to slide within the lumen 26 of the cannula 12 in a second rotational orientation that is offset from the first rotational orientation by angle 37. Accordingly, the electrode array carried at the distal end 16 of the shaft 14 can have two operative positions or orientations that correspond with the orientations of the keyways 34a and 34b of the indexer 22a. As will be described in further detail below, the designed magnitude of the angle 37 will depend on the number of wires 21.

The distance through which the index-key 24a longitudinally travels within either of the keyways 34a and 34b of the indexer 22a may vary. In the illustrated embodiment, the indexer 22a has a length 31, such that the shaft 14 is rotationally guided by the indexer 22a until the wires 21 at the distal end 16 of the shaft 14 are completely deployed. Alternatively, the shaft 14 may be rotationally guided by the indexer 22a only during the initial deployment range of the wires 21. In certain clinical situations or procedures, guiding the shaft 14 through the complete deployment range of the wires 21 may not be necessary. For example, once a portion of each of the wires 21 is deployed into a target tissue, the distal end 16 of the shaft 14 becomes rotatably secured, at least to a certain extent, by the tissue. As such, any further advancement of the shaft 14 could be guided by the tissue without the help of the angle indexing apparatus 19.

Figure 5:
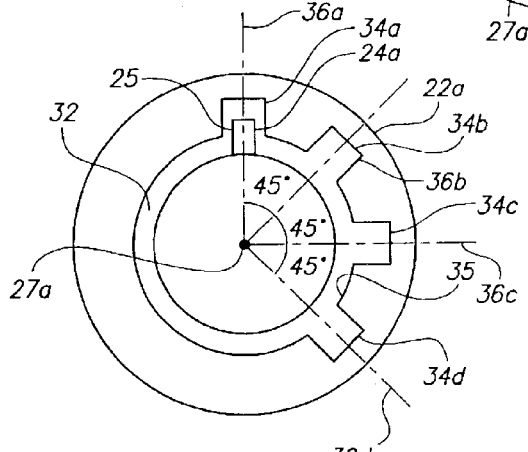
FIG. 5 is a cross sectional view of a variation of the angle indexing apparatus of FIG. 4, particularly showing the indexer having more than two keyways.

Although the previously described indexer 22a includes two keyways 34, the number of keyways and the angle formed between the keyways may vary, depending on the particular application or clinical procedure. FIG. 5 shows a variation of the indexer 22a that includes four keyways 34a–34d located on radial lines 36a–d, respectively. The radial line 36b is 45° from the radial line 36a, the radial line 36c is 45° from the radial line 36b, and the radial line 36d is 45° from the radial line 36c. As such, each of the radial lines 36 is evenly spaced from the adjacent radial line. Alternatively, the radial lines 36 can be spaced unevenly. The shaft 14 can be guided to slide within the lumen 26 of the cannula 12 in four fixed rotational orientations by fitting the key element 25 of the index-key 24a within any one of the keyways 34a–34d.

Having just described the structure of the probe assembly 10, its operation in performing multiple ablations will now be described with reference to FIGS. 6A–6D. In this example, the indexer 22a illustrated in FIG. 4 is used, and the probe assembly 10 includes a two-wire array having wires 21a and 21b. In particular, the indexer 22a has two keyways 34a and 34b separated by an angle 37 of 90°.

Figure 6A:
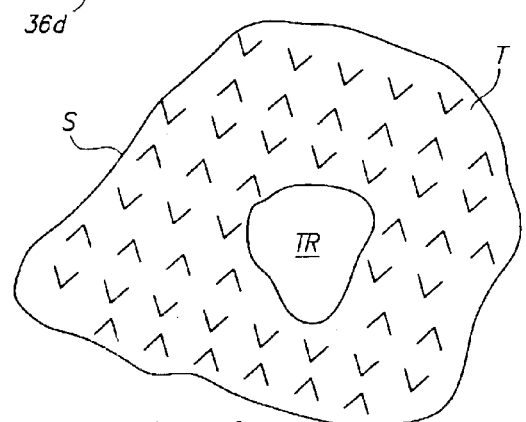
FIGS. 6A–6D illustrates cross-sectional views of one preferred method of using the probe assembly of FIG. 2 to treat tissue.
Figure 6B:
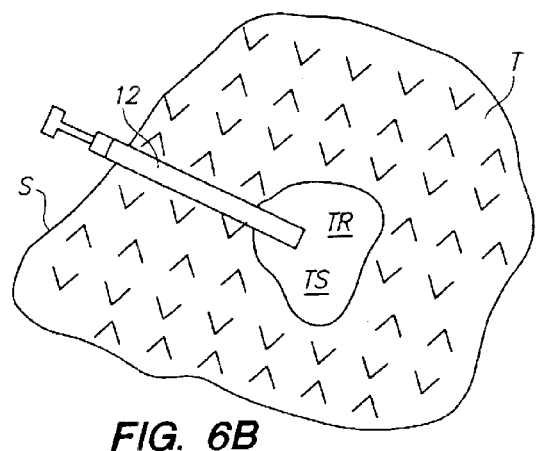

Referring now to FIGS. 6A–6D, the operation of the probe assembly 10 is described in treating a treatment region TR within a tissue located beneath the skin or an organ surface S of a patient. The tissue T prior to treatment is shown in FIG. 6A. The cannula 12 is first introduced within the treatment region TR, so that the distal end of the cannula 12 is located at the target site TS, as shown in FIG. 6B. This can be accomplished using any one of a variety of techniques. In some cases, the cannula 12 and shaft 14 may be introduced to the target site TS percutaneously directly through the patient's skin or through an open surgical incision. In this case, the cannula 12 may have a sharpened tip, e.g., in the form of a needle, to facilitate introduction to the treatment region. In such cases, it is desirable that the cannula 12 or needle be sufficiently rigid, i.e., have a sufficient column strength, so that it can be accurately advanced through tissue. In other cases, the cannula 12 may be introduced using an internal stylet that is subsequently exchanged for the shaft 14 that carries the wires 21. In this latter case, the cannula 12 can be relatively flexible, since the initial column strength will be provided by the stylet. More alternatively, a component or element may be provided for introducing the cannula 12 to the treatment region. For example, a conventional sheath and sharpened obturator (stylet) assembly can be used to initially access the target site. The assembly can be positioned under ultrasonic or other conventional imaging, with the obturator/stylet then removed to leave an access lumen through the sheath. The cannula 12 and shaft 14 can then be introduced through the sheath lumen, so that the distal end of the cannula 12 advances from the sheath into the target site TS.

Figure 6C:
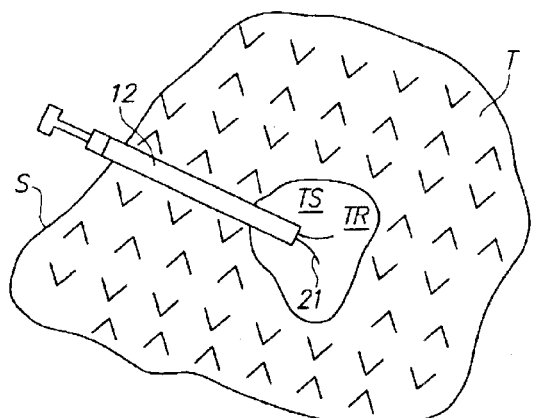
Figure 6D:
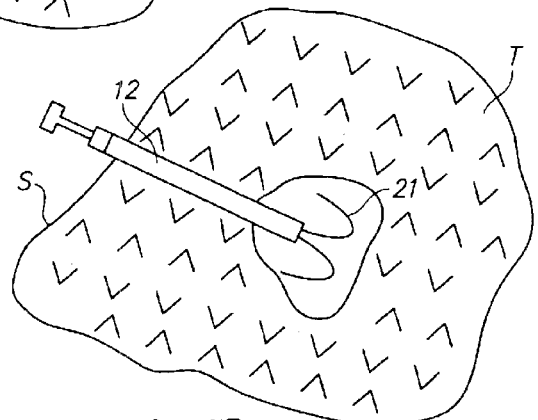

After the cannula 12 is properly placed, the shaft 14 is distally advanced until the index-key 24a is mated with the indexer 22a, thereby guiding the wires 21 to deploy radially outward from the distal end of the cannula 12, as shown in FIG. 6C. The shaft 14 will be advanced sufficiently, so that the wires 21 fully deploy in order to circumscribe substantially the entire treatment region TR, as shown in FIG. 6D.

Figures 7A, 7B, 8:
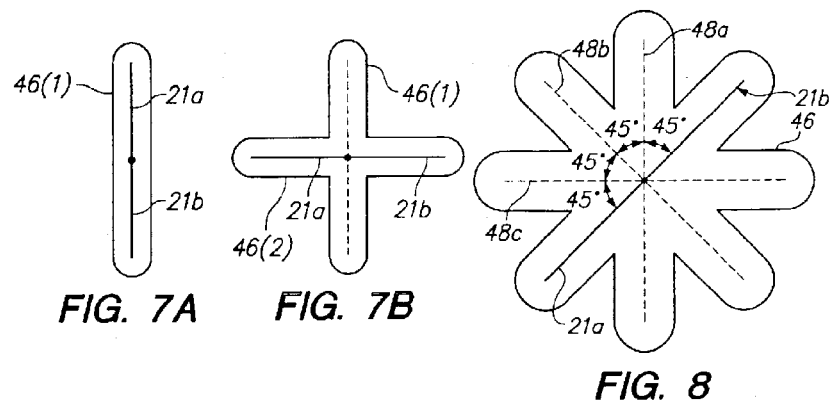
FIG. 7A is an end view of a probe assembly having two spreading wires spaced at 180°.
FIG. 7B is an end view of the probe assembly of FIG. 7A, particularly showing the position of the wires that have been rotated 90°.
FIG. 8 is an end view of the probe assembly of FIG. 7A, particularly showing the position of the wires that have been rotated 45° three times.

FIG. 7A shows the wires 21a and 21b in a first deployed position when the index-key 24a is mated with the keyway 34a of the indexer 22a. While in their first deployed position, the wires 21a and 21b deliver ablation energy to create a lesion 46(1) at a target tissue. If it is desired that the wires 21a and 21b be deployed in a second position, the wires 21a and 21b are first retracted into the lumen 26 of the cannula 12 until the index-key 24a becomes disengaged with the first keyway 34a of the indexer 22a. The proximal end 18 of the shaft 14, or the handle 28 if one is provided, is then rotated until the index-key 24a is at a position at which a distal advancement of the shaft 14 would bring the index-key 24a into the second keyway 34b of the indexer 22a. The shaft 14 is then advanced distally until the index-key 24a engages with the second keyway 34b of the indexer 22a. The shaft 14 is then further advanced until the wires 21a and 21b are partially or completely deployed at the distal end of the cannula 12. Once the wires 21a and 21b are in the second deployed position, ablation energy can be delivered to the wires 21a and 21b to create a lesion 46(2) at a different region of the target tissue. FIG. 7B shows that the wires 21a and 21b are deployed in a second position that is approximately 90° from the first position, thereby forming a lesion pattern having four branches that are substantially evenly spaced.

If the indexer 22a of FIG. 5 (having four keyways 34) is used, the wires 21a and 21b can be deployed in four different positions by mating the index-key 24a within the keyways 34a–34d, respectively, of the indexer 22a. FIG. 8 shows the various rotational orientations of the wires 21a and 21b when the shaft 14 is repositioned such that the index-key 24a is mated with the four keyways 34a–d of the indexer 22a. Dash lines 48a, 48b and 48c represent the positions of the wires 21a and 21b when the index-key 24a is mated with the keyways 34a, 34b and 34c, respectively, of the indexer 22a. The solid line shown in FIG. 8 represents the fourth and current position of the wires 21a and 21b when the index-key 24a is mated with the keyway 34d of the indexer 22a. As such, by deploying the wires 21a and 21b at different positions to ablating different regions of the target tissue, a more complete and uniform lesion 46 can be created, as illustrated in FIG. 8.

Figures 9A, 9B:
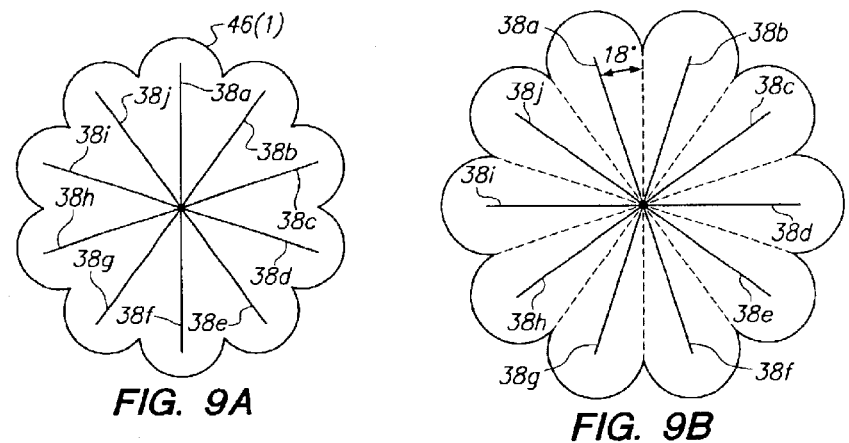
FIG. 9A is an end view of a probe assembly having ten spreading wires spaced at 36°.
FIG. 9B is an end view of the probe assembly of FIG. 9A, particularly showing the position of the wires that have been rotated 18°.

As another example, the indexer 22a illustrated in FIG. 4 can be used with an ablation probe that includes a ten-wire array having wires 38a–38j spaced at substantially even intervals, i.e., 36°. In this case, the angle 37 between the keyways 34a and 34b of the indexer 22a is 18°. In the manner similarly described above, the shaft 14 is inserted within the cannula 12, index-key 24a is aligned and mated with the keyway 34a of the indexer 22a, and the shaft 14 is advanced through the cannula 12 until the wires 38a–38j are fully deployed within the target tissue (FIG. 9A). Ablation energy is then delivered to the target tissue to form a lesion 46(1). The wires 38 are then retracted into the lumen 26 of the cannula 12 until the index-key 24a becomes disengaged with the first keyway 34a of the indexer 22a. The proximal end 18 of the shaft 14, or the handle 28 if one is provided, is then rotated until the index-key 24a is at a position at which a distal advancement of the shaft 14 would bring the index-key 24a into the second keyway 34b of the indexer 22a. The shaft 14 is then advanced distally until the index-key 24a engages with the second keyway 34b of the indexer 22a. The shaft 14 is further advanced until the wires 38 are partially or completely deployed at the distal end of the cannula 12. FIG. 9B shows the first deployed position (in dashed lines) and the second deployed position of the wires 38a–j after they have been rotated 18°. Each of the wires 38a–j in the second deployed position is substantially at midpoint between the first deployed position of two of the wires 38a–j. Once the wires 38 are in the second deployed position, ablation energy can be delivered to the wires 38 to create a lesion 46(2) at a different region of the target tissue.

As shown in FIGS. 7–9, depending on the number of wires 21 that the device 10 contains, and the number of adjustable positions for the wires 21 desired, the angle 37 between the corresponding radial lines 36 of the keyways 34 (see FIGS. 4 and 5) can be selected, such that deployment of the wires 21 in the various respective positions could provide a substantially complete and uniform ablation coverage of the target tissue. Alternatively, the angle 37 between the radial lines 36 can be selected based on other criteria, such as the geometry or location of the target tissue.

Figure 10:
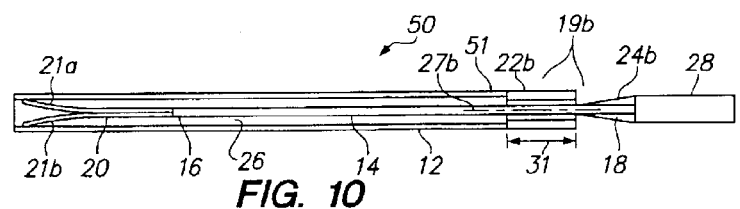
FIG. 10 is a side cross sectional view of a an angle indexing apparatus in accordance with another preferred embodiment of the present invention.
Figure 11:
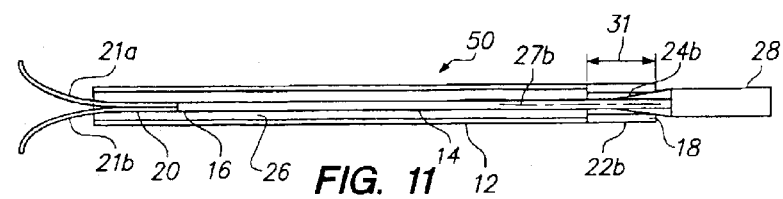
FIG. 11 is a side cross sectional view of the probe assembly of FIG. 10, particularly showing the wires deployed at the distal end of the cannula.

Referring now to FIG. 10, a probe assembly 50 constructed in accordance with another preferred embodiment of the present inventions is described. The probe assembly 50 is similar to the previously described probe assembly 10, with the exception that it comprises an index-key 24b that includes a sleeve 52, which is capable of being secured to the shaft 14. The probe assembly 50 further includes an indexer 22b having an axis 27b, and an index-key 24b that is capable of mating with the indexer 22b in at two positions. As shown in FIG. 11, the index-key 24b is mated with the indexer 22b when the shaft 14 is advanced to deploy the wires 21a and 21b at the distal end 16 of the shaft 14.

Figure 12:
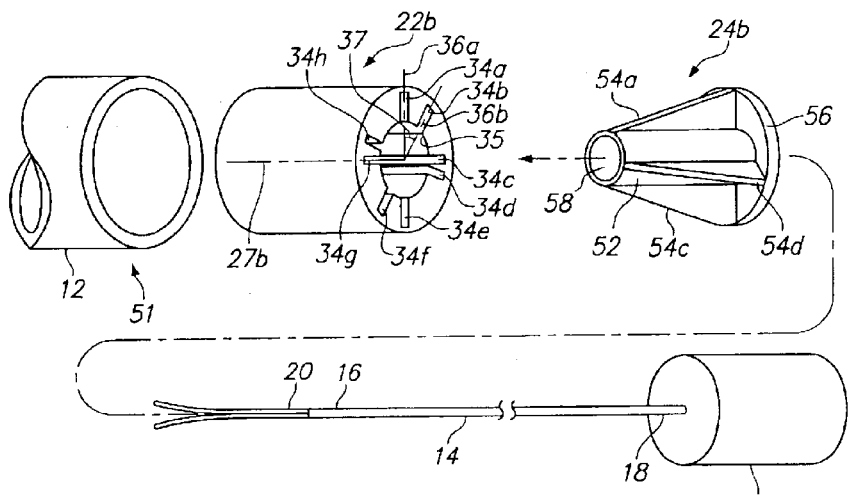
FIG. 12 is a perspective view of the probe assembly of FIG. 11, particularly showing how the indexer and index-key are coupled to the cannula and shaft, respectively.

Turning to FIG. 12, the indexer 22b has an interior surface 35 defining a bore 32, and a plurality of keyways 34a–h. Each of the keyways 34 is located along a corresponding radial line 36. As discussed previously, the indexer 22b can be secured to the proximal end of the cannula 12 by a variety of mechanisms, such as luer-type connection, friction-type connection, welding, glue, or screws. The sleeve 52 of the index-key 24b has a bore 58, and four equally spaced radially extending key elements 54 secured to the exterior surface of the sleeve 52. As illustrated in FIG. 12, the key elements 54 may be fins. Alternatively, the key elements 54 may be pins, pegs, or other projections secured to the surface of the sleeve 52. Although not required, the index-key 24b optionally includes a disk 56 secured to a proximal end of the sleeve 52 and the key elements 54 for the purpose of strengthening or stiffening the key elements 54.

The sleeve 52 of the index-key 24b is adapted to coaxially secure the shaft 14 to the index-key 24b. In a preferred embodiment, the diameter of the bore 58 is made sufficiently small so that the sleeve 52 acts as a friction-type connection. Alternatively, the inner surface of the sleeve 52 and the proximal end 18 of the shaft 14 may include screw-threads, and the index-key 24b is then secured to the shaft 14 by screwing the shaft 14 into the threaded sleeve 58 of the index-key 24b. As a further alternative, the bore 58 may have a diameter that is slightly larger than the diameter of the shaft 14, and the index-key 24b is then secured to the shaft 14 by bonding the interior surface of the sleeve 52 to the proximal end 18 of the shaft 14. The optional proximal disk 56 can then be secured to the distal face of the handle 28 by using glue or other appropriate adhesives. It should be noted that regardless of the type of connection used to secure the index-key 24b to the shaft 14, the index-key 24b should be rigidly secured to the shaft 14 so that the index-key 24b cannot coaxially rotate relative to the shaft 14. An advantage of using the index-key 24b shown in FIG. 12 is that the index-key 24b can readily be used with existing devices without the need of modifying the devices.

As illustrated in FIG. 12, the four key elements 54a–d (key element 54d not shown) of the index-key 24b are adapted to respectively fit within the keyways 34a, 34c, 34e, and 34g of the indexer 22b, while guiding the shaft 14 to slide within the lumen 26 of the cannula 12 in one orientation. The key elements 54a–d are adapted to respectively fit within the keyways 34b, 34d, 34f, and 34h of the indexer 22b, while guiding the shaft 14 to slide within the lumen 26 of the cannula 12 in a second orientation. As discussed previously, the number of key elements 54 and keyways 34 may vary. Furthermore, the indexer 22b may have a sufficient number of keyways 34 such that it allows the shaft 14 to be operated relative to the cannula 12 in more than two orientations.

Figure 13:
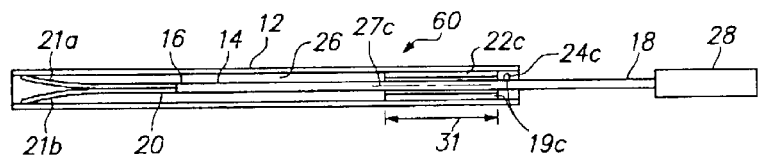
FIG. 13 is a side cross sectional view of a probe assembly having an angle indexing apparatus in accordance with another preferred embodiment of the present invention.
Figure 14:
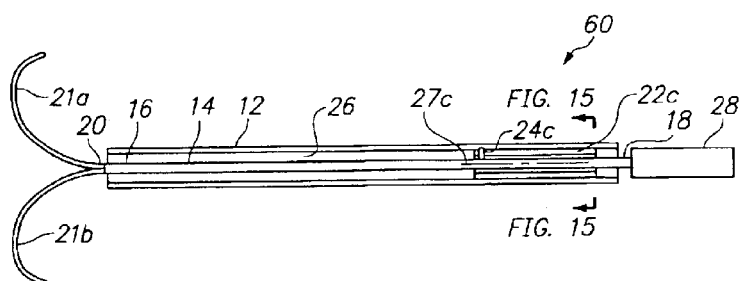
FIG. 14 is a side cross sectional view of the probe assembly of FIG. 13, particularly showing the wires deployed at the distal end of the cannula.
Figure 15:
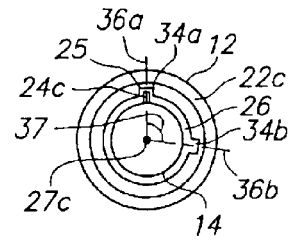
FIG. 15 is a cross sectional view of the probe assembly of FIG. 14, particularly showing the index-key mated with the indexer.

In all the previously described embodiments, the indexer 22 is secured or configured to be secured to the proximal end of the cannula 12. However, the indexer 22 can also be secured to other part(s) of the cannula 12. Referring now to FIGS. 13–15, a probe assembly 60 constructed in accordance with still another preferred embodiment of the present inventions is described. The probe assembly 60 is similar to the previously described probe assembly 10, with the exception that the indexer 22 is secured within the lumen 26 of the cannula 12. In the illustrated embodiment, the indexer 22c is secured to the proximal end of the cannula, but can be secured within the distal end or anywhere along the cannula. The indexer 22c is preferably secured to the cannula 12 by a friction-type connection. Alternatively, the indexer 22c may be detachably secured to the cannula 12 by a screw connection, or permanently secured to the cannula 12 by welding, brazing, glue, or other suitable adhesive.

Referring specifically, to FIG. 15, the index-key 24c has a single key element 25, and is configured to mate with the indexer 22c when the shaft 14 is advanced to deploy the wires 21a and 21b (FIG. 14). The indexer 22c has two keyways 34a and 34b for mating with the index-key 24c, so that the shaft 14 can be guided to slide within the lumen 26 of the cannula 12 in one orientation when the key element 25 of the index-key 24c is fitted within the first keyway 34a, and in a second orientation when the key element 25 of the index-key 24c is fitted within the second keyway 34b. Each of the keyways 34 lies along a corresponding radial line 36.

Figure 16:
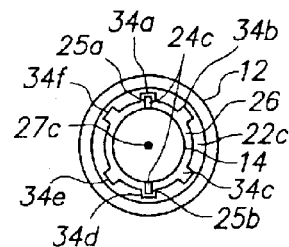
FIG. 16 is a cross sectional view of a variation of the angle indexing apparatus of FIG. 15, particularly showing the index-key having more than two adjustable positions relative to the indexer.

As discussed previously, the number and location of the keyways 34 may vary. The number of key elements 25 of the index-key 24c may also vary. For example, FIG. 16 shows a variation of the indexer 22c and index-key 24c. The indexer 22c includes six keyways 34a–f, and the index-key 24c has two key elements 25a and 25b. The key elements 25a and 25b are adapted to mate with two of the keyways 34a–f when the shaft 14 is being guided to slide within the lumen 26 of the cannula 12 in one orientation. In particular, FIG. 16 shows that the key elements 25a and 25b are respectively fitted within the keyways 34a and 34d of the indexer 22c. If it is desired to deploy the wires 21a and 21b in a second position, the shaft 14 is then retracted and rotated such that the keys 25a and 25b fit within the keyways 34b and 34e, respectively, of the indexer 22c. If it is desired to deploy the wires 21a and 21b in a third position, such can be accomplished by respectively fitting the keys 25a and 25b within the keyways 34c and 34f of the indexer 22c. The number of deployed positions for the wires 21 depends on the number of keys 25 and the number of keyways 34. FIG. 16 shows that the key 25a is located at 180° from the key 25b. Alternatively, the key 25a and the key 25b may be located from each other at a different angle.

Figure 17:
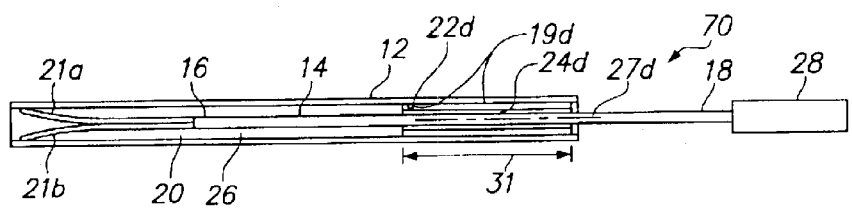
FIG. 17 is a side cross sectional view of a probe assembly having an angle indexing apparatus in accordance with another preferred embodiment of the present invention.
Figure 18:
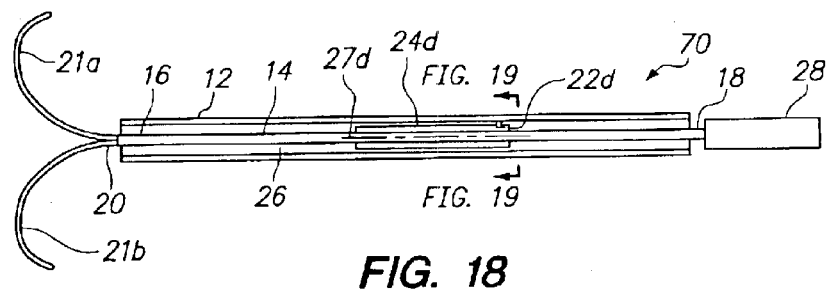
FIG. 18 is a side cross sectional view of the probe assembly of FIG. 17, particularly showing the wires deployed at the distal end of the cannula.
Figure 19:
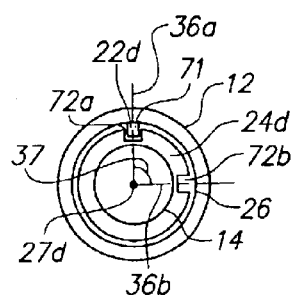
FIG. 19 is a cross sectional view of the probe assembly of FIG. 18, particularly showing the index-key mated with the indexer.

In all the examples discussed previously, it is the indexer 22 that includes the keyways 34, and it is the index-key 24 that includes the key(s) 25. However, the indexer 22 is not limited to having keyways and the index-key 24 is not limited to having key elements, so long as the index-key 24 is capable of mating with the indexer 22. Referring now to FIGS. 17–19, a probe assembly 70 constructed in accordance with still another preferred embodiment of the present inventions is described. The probe assembly 70 is similar to the previously described probe assembly 10, with the exception that the indexer 22 has key element(s) instead of keyways, and the index-key 24 has keyways instead of key element(s).

In particular, the probe assembly 70 includes an indexer 22d having one key element 71, and an index-key 24d having two keyways 72a and 72b. The key element 71 of the indexer 22d is preferably a projection, such as a pin, a peg, or a fin, that is secured to, or manufactured as a single unit with, an interior surface of the cannula 12. The index-key 24d has a tubular shape and an axis 27d, and is secured to the proximal end 18 of the shaft 14. Alternatively, the index-key 24d may be secured to the distal end 16 or anywhere along the shaft 14. The keyways 72 of the index-key 24d are located at an interior surface of the index-key 24d. The index-key 24d is configured to mate with the indexer 22d when the shaft 14 is advanced to deploy the wires 21a and 21b (FIG. 18). As shown in FIG. 19, the keyways 72a and 72b lie along corresponding radial lines 36a and 36b, which define an angle 37. The shaft 14 can be guided to slide within the lumen 26 of the cannula 12 in one orientation when the first keyway 72a of the index-key 24d is mated with the key element 71 of the indexer 22d, and in a second orientation when the second keyway 72b is mated with the key element 71 of the indexer 22d.

Figure 20:
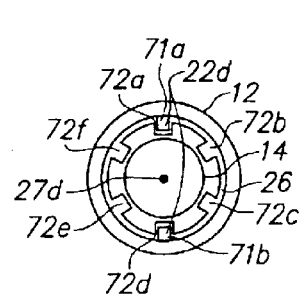
FIG. 20 is a cross sectional view of a variation of the angle indexing apparatus of FIG. 19, particularly showing the index-key having more than two adjustable positions relative to the indexer.

Although the illustrated embodiment of FIG. 19 shows that the index-key 24d includes two keyways 72 and the indexer 22d includes one key element 71, the number of keyways and key elements and the angle formed between the keyways may vary, depending on the particular application or clinical procedure. For example, FIG. 20 shows a variation of the indexer 22d and the index-key 24d. The indexer 22d includes two projections 71a and 71b, and the index-key 24d includes six keyways 72a–f. As FIG. 20 shows, the projections 71a and 71b of the indexer 22d fits within the keyways 72a and 72d of the index-key 24d when the shaft 14 is guided to slide within the cannula 12 in a first orientation, thereby deploying the wires 21a and 21b in a first position. If it is desired to deploy the wires 21a and 21b in a second position, the shaft 14 is first retracted. The shaft 14 is then rotated and advanced such that the projections 71a and 71b of the indexer 22d fit within the keyways 72b and 72e (or 72c and 72f) of the index-key 24d, thereby, deploying the wires 21a and 21b in a second position.

Figure 21:
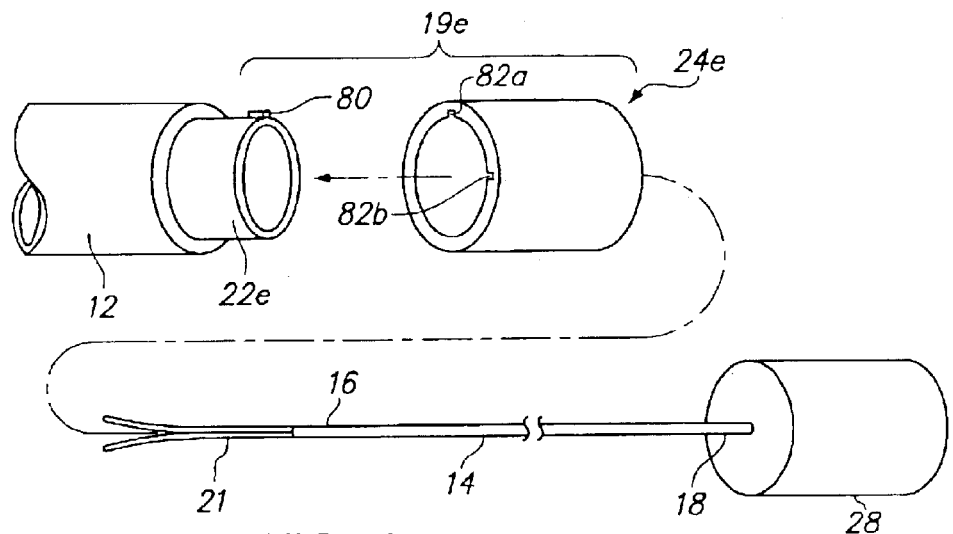
FIG. 21 is a perspective view of another variation of the angle indexing apparatus, particularly showing the indexer configured to fit within the index-key.

In all the examples discussed previously, the index-key 24 is mated within the indexer 22. The indexer 22, however, can instead be mated within the index-key 24. Referring now to FIG. 21, a probe assembly 80 constructed in accordance with still another preferred embodiment of the present inventions is described. The probe assembly 80 is similar to the previously described probe assembly 70, with the exception that the indexer 22 is configured to fit within the index-key 24.

In particular, the probe assembly 80 includes an indexer 22e having one key element 80, and an index-key 24e having two keyways 82a and 82b. The key element 80 of the indexer 22e is preferably a projection, such as a pin, a peg, or a fin, that is secured to, or manufactured as a single unit with, an exterior surface of the cannula 12. The index-key 24e has a tubular shape and an axis 27d, and is secured to the proximal end 18 of the shaft 14. The keyways 82 of the index-key 24e are located at an interior surface of the index-key 24e. The key element 80 of the indexer 22e is configured to fit within one of the keyways 82 of the index-key 24e when the index-key 24e is slid to fit around the indexer 22e.

Figure 22:
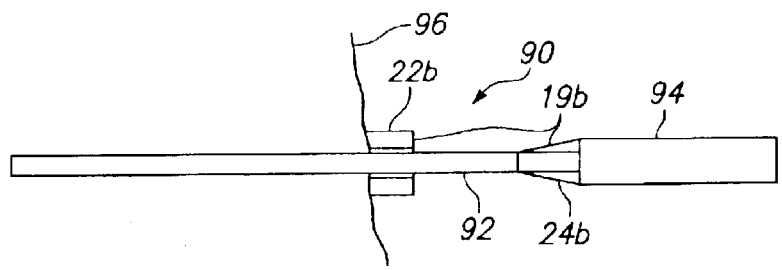
FIG. 22 is a side view of a probe assembly, particularly showing the indexer secured to a skin of a patient.

Each of the indexers 22 described previously is secured to the cannula 12 during use of the ablation device. It should be noted, however, that the indexer 22 may also be secured to a patient or other object, such as an operation table or another medical instrument, as long as the indexer 22 is secured in a position relative to which the shaft 14 can move. For example, FIG. 22 shows a probe assembly 90 that is similar to the previously described probe assembly 50, with the exception that it does not use a cannula. Rather, the shaft 12 is directly percutaneously introduced into the body of the patient. In this case, the indexer 22b is secured to the skin 96 of the patient, e.g., by the use of surgical tape, biomaterial adhesive, belt, or stitches. Alternatively, the indexer 22b can be held in position by the physician or assistant. As with the probe assembly 50, the index-key 24b is secured to the shaft 12 or the handle 28. The index-key 24b is adapted to mate with the indexer 22b in a number of positions, as previously described in the probe assembly 50. As such, the probe assembly 90 can be predictably and accurately operated in a number of positions, as discussed previously.

Figure 23:
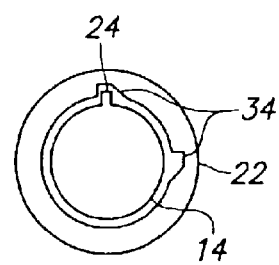
FIG. 23 is a cross sectional view of yet another variation of the angle indexing apparatus.

The indexer 22 and the index-key 24 of the angle indexing apparatus 19 are not limited to those described previously, and may have other shapes and configurations, so long as the index-key 24 is capable of mating with the indexer 22 in a plurality of positions. For example, as shown in FIG. 23, the keyway 34 of the indexer 22 may have a shape that allows the index-key 24 to be rotated into a second position without requiring changing the longitudinal position of the index-key 24 relative to the indexer 22. Keyway 34 and index-key 24 having other shapes may also be used.

It should also be noted that the operative element 20 is not limited to wires that delivery ablation energy. The operative element 20 can be a variety of instruments such as sensors, cutting devices, mapping instruments, embolic devices, or delivery devices. Although the indexer 22 and the index-key 24 were discussed previously with reference to a probe assembly or other medical devices, it is intended that the indexer 22 and the index-key 24 can also be fabricated separately from the medical device, and are then incorporated into an existing or pre-fabricated medical device.

Thus, although several preferred embodiments have been shown and described, it would be apparent to those skilled in the art that many changes and modifications may be made thereunto without the departing from the scope of the invention, which is defined by the following claims and their equivalents.

What is claimed:

1. A medical device, comprising:
    a tubular element;
    an elongate member having a proximal end and a distal end;
    an operative element carried at the distal end of the elongate member;
    an indexer; and
    an index-key coupled to a cone-shaped intermediate element, the cone-shaped intermediate element having a bore and a radially extending key element secured to the exterior of the coe-shaped intermediate element, the cone-shaped intermediate element being configured to secure the elongate member to the index-key, wherein the index-key is adapted to mate with the indexer in at least two fixed rotational positions.

2. The medical device of claim 1, wherein the index-key is secured to a proximal end of the elongate member.

3. The medical device of claim 1, wherein one of the indexer and index-key has at least two keyways, and another of the indexer and index-key has at least one key element adapted to mate with each of the at least two keyways.

4. The medical device of claim 3, wherein the at least two keyways comprises only two keyways, and the at least one key element comprises only one key element.

5. The medical device of claim 3, wherein the at least two keyways comprises at least four keyways, and the at least one key element comprises at least two key elements.

6. The medical device of claim 3, wherein the at least two keyways lie along two radial lines that define one or more angles equal to or less than 90°.

7. The medical device of claim 1, wherein the index-key is adapted to fit within the indexer.

8. The medical device of claim 1, wherein the indexer is configured to fit within the index-key.

9. The medical device of claim 1, wherein the elongate member is slidable within a lumen of the tubular element.

10. The medical device of claim 1, wherein the indexer is secured to a proximal end of the tubular element.

11. The medical device of claim 1, wherein the indexer is adapted to be hand-held by an operator.

12. The medical device of claim 1, further comprising a handle coupled to a proximal end of the elongate member, wherein the index-key is secured to the handle.

13. The medical device of claim 1, wherein the operative element is a needle electrode array.

14. The medical device of claim 13, wherein the needle electrode array comprises at least two wires that are substantially equally spaced when fully deployed.

15. The medical device of claim 14, wherein the at least two wires are placed in first positions when the index key is mated with the indexer in the first rotational position, and placed in second positions when the index key is mated with the indexer in the second rotational position, and wherein the first positions are substantially midway between the second positions.

16. An angle indexing apparatus for positioning a medical device in a plurality of orientations, comprising:
    an index-key configured for coupling to the medical device; and
    an indexer securable in a position relative to which the index-key can move;
    wherein the index-key is coupled to a cone-shaped intermediate element, the cone-shaped intermediate element having a bore and a radially extending key element secured to the exterior of the cone-shaped intermediate element, the cone-shaped intermediate element being configured to secure an operative element to the index-key and to mate the indexer with the index-key in at least two fixed rotational orientations.

17. The apparatus of claim 16, wherein one of the indexer and index-key has at least two keyways, and another of the indexer and index-key has at least one key element adapted to mate with each of the at least two keyways.

18. The apparatus of claim 17, wherein the at least two keyways comprises only two keyways, and the at least one key element comprises only one key element.

19. The apparatus of claim 17, wherein the at least two keyways comprises at least four keyways, and the at least one key element comprises at least two key elements.

20. The apparatus of claim 17, wherein the at least two keyways lie along two radial lines that define one or more angles equal to or less than 90°.

21. The apparatus of claim 16, wherein the index-key is adapted to fit within the indexer.

22. The apparatus of claim 16, wherein the indexer is configured to fit within the index-key.

23. The apparatus of claim 16, wherein the indexer is configured for coupling to the tubular element of the medical device.

24. The apparatus of claim 16, wherein the indexer is adapted to be hand-held by an operator.

* * * * *